United States Patent [19]

Ohashi et al.

[11] Patent Number: 5,210,251
[45] Date of Patent: May 11, 1993

[54] ESTER-MODIFIED SILICONE DERIVATIVE AND A COSMETIC COMPOSITION CONTAINING THE SAME

[75] Inventors: Yukihiro Ohashi; Ken Takeuchi; Mituo Suda; Koji Yoshino; Akira Kawamata, all of Tochigi; Yoko Mastui; Yuji Suzuki, both of Chiba, all of Japan

[73] Assignee: Kao Corporation, Tokyo, Japan

[21] Appl. No.: 668,646

[22] Filed: Mar. 13, 1991

[30] Foreign Application Priority Data

Mar. 15, 1990 [JP] Japan ................................. 2-65433

[51] Int. Cl.$^5$ ............................................. C07F 7/08
[52] U.S. Cl. ............................. 556/437; 424/64; 424/70; 424/71
[58] Field of Search ................ 556/437; 424/64, 70, 424/71

[56] References Cited

U.S. PATENT DOCUMENTS

| | | | |
|---|---|---|---|
| 3,398,104 | 8/1968 | Haluska | 556/437 X |
| 3,402,192 | 9/1968 | Haluska | 260/448.2 |
| 3,427,271 | 2/1969 | McKellar | 556/437 X |
| 3,518,288 | 6/1970 | Haluska | 556/437 X |
| 4,687,786 | 8/1987 | Kollmeier et al. | 556/437 X |
| 4,847,398 | 7/1989 | Mehta et al. | 556/437 X |
| 4,853,474 | 8/1989 | Bahr et al. | 556/437 X |

FOREIGN PATENT DOCUMENTS

| | | |
|---|---|---|
| 0075703 | 4/1983 | European Pat. Off. |
| 0193815 | 9/1986 | European Pat. Off. |
| 0252878 | 1/1988 | European Pat. Off. |
| 0310903 | 4/1989 | European Pat. Off. |
| 0362860 | 4/1990 | European Pat. Off. |
| 3622571 | 1/1988 | Fed. Rep. of Germany |
| 955916 | 4/1964 | United Kingdom |

*Primary Examiner*—Paul F. Shaver
*Attorney, Agent, or Firm*—Sughrue, Mion, Zinn, Macpeak & Seas

[57] ABSTRACT

An ester-modified silicone derivative of formula (I):

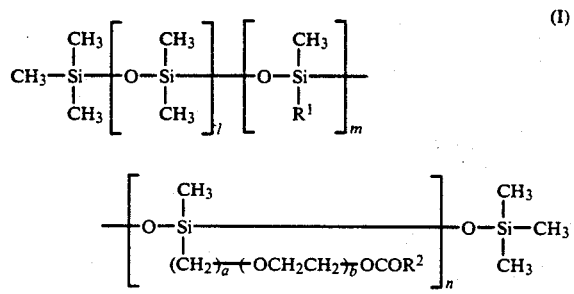

wherein $R^1$ and $R^2$ are the same or different and each represents a saturated or unsaturated straight- or branched-chain aliphatic hydrocarbon group having from 2 to 30 carbon atoms, a saturated or unsaturated alicyclic hydrocarbon group having from 3 to 30 carbon atoms or an aromatic hydrocarbon group having from 6 to 30 carbon atoms; l and m each represents a number of 0 to 100; n represents a number of 1 to 100; a represents a number of 3 to 16; and b represents a number of 1 to 3 is disclosed as well as a cosmetic composition containing the ester-modified silicone derivative.

2 Claims, No Drawings

ESTER-MODIFIED SILICONE DERIVATIVE AND A COSMETIC COMPOSITION CONTAINING THE SAME

FIELD OF THE INVENTION

The present invention relates to a novel ester-modified silicone derivative and a cosmetic composition containing the same.

BACKGROUND OF THE INVENTION

Silicone oil has excellent lubricating properties, water repellency, gloss-imparting property, shelf stability and safety and as such is used widely as a cosmetic base.

However, high molecular weight dimethylpolysiloxanes, one of the silicone oils which is most commonly in use, is sparingly soluble in polar oils and water and is hardly emulsifiable in hydrocarbon oil-containing systems. Furthermore, cosmetic products containing this silicone oil and other silicone oils give characteristic "squeak" and thus are unsatisfactory in feel.

There has, accordingly, been a long-standing demand for the development of a silicone derivative which insures an improved feeling in use which the conventional silicone oils lack.

Under these circumstances the inventors of the present invention explored the above problem and found that an ester-modified silicone derivative of formula (I) shown below is highly compatible with hydrocarbon oils, polar oils, water, etc., and remains stable in systems containing the same and further that cosmetic formulations including this compound does not give "squeak", thus offering an improved feeling in use. The present invention is based on the above finding.

SUMMARY OF THE INVENTION

The present invention relates, in one aspect, to an ester-modified silicone derivative of formula (I):

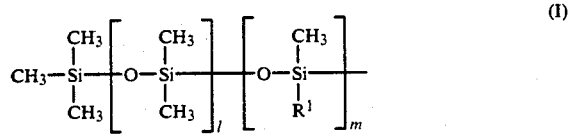

wherein $R^1$ and $R^2$ are the same or different and each represents a saturated or unsaturated, straight- or branched-chain aliphatic hydrocarbon group having from 2 to 30 carbon atoms, a saturated or unsaturated alicyclic hydrocarbon group having from 3 to 30 carbon atoms or an aromatic hydrocarbon groups having from 6 to 30 carbon atoms; l and m is each represents a number of from 0 to 100; n represents a number of from 1 to 100; a represents a number of from 3 to 16; and b represents a number of from 1 to 3.

In another aspect, the present invention relates to a cosmetic composition containing the ester-modified silicone derivative.

DETAILED DESCRIPTION OF THE INVENTION

Referring to formula (I), the hydrocarbon group represented by $R^1$ includes, for example, ethyl, propyl, butyl, isobutyl, pentyl, hexyl, heptyl, octyl, nonyl, decyl, dodecyl, tetradecyl, hexadecyl, octadecyl, dodecyl, phenyl and so on. The group —$OCOR^2$ includes various carboxylic acid residues such as residues of acetic acid, butyric acid, capric acid, lauric acid, myristic acid, palmitic acid, stearic acid, behenic acid, melissic acid, palmitoleic acid, oleic acid, linolic acid, linolenic acid, arachidonic acid, erucic acid, 2-ethylhexanoic acid, 2-hexyldecanoic acid, 2-heptylundecanoic acid, 5,7,7-trimethyl-2-(1,3,3-trimethylbutyl)octanoic acid, methyl-branched isostearic acid, cyclopentanecarboxylic acid, cyclohexanecarboxylic acid, abietic acid, dehydroabietic acid, dehydroabietic acid, tetrahydroabietic acid, cholic acid, deoxycholic acid, glycyrrhizic acid, benzoic acid, naphthoic acid and so on. As the hydrocarbon group represented by $R^1$ or $R^2$, those having from 6 to 22 carbon atoms are preferred, and phenyl group is more preferred.

In formula (I) above, l preferably represents a number of from 10 to 100, m preferably represents a number of from 0 to 30, n preferably represents a number of from 2 to 20 and a preferably represents a number of from 3 to 11.

The molecular weight of the methylpolysiloxane moiety is preferably not more than 9,000.

The ester-modified silicone derivative (I) of the present invention can be synthesized by various processes including the following processes.

Process A

A hydrogenpolysiloxane (II) and an ester (III) are reacted in the presence of a catalytic amount of chloroplatinic acid catalyst at room temperature or under heating to give an ester-modified silicone derivative (I).

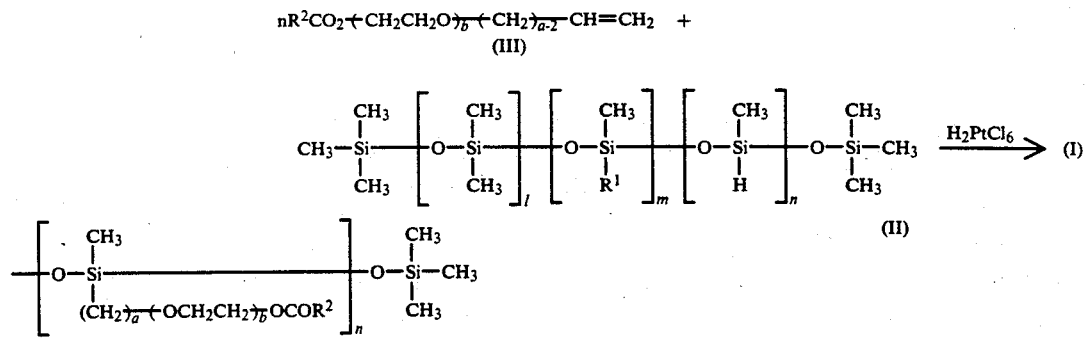

wherein $R^1$, $R^2$, a, b, l, m and n have the meanings respectively defined hereinbefore.

The starting material ester (III) can be easily synthesized, for example, by reacting a carboxylic acid or a reactive derivative, e.g., a chloride, thereof (IV), with an alcohol (V) in a known manner, as follows.

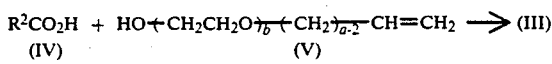

wherein $R^2$, a and b have the same meanings as respectively defined hereinbefore.

The hydrogenpolysiloxane of formula (II) wherein m is equal to 0 is commercially available, for example, from Toshiba Silicone Co., Ltd., and those of formula (II') wherein m is not equal to 0 can be produced, for example, by reacting a hydrogenpolysiloxane of formula (VI) with an olefin of formula (VII) in the presence of a catalytic amount of chloroplatinic acid catalyst, as follows.

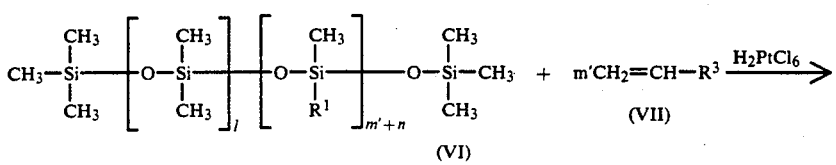

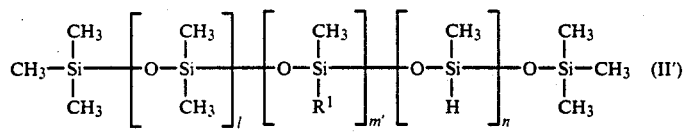

wherein $R^1$, l and n have the meanings respectively defined hereinbefore; m' represents an integer of from 1 to 100; and $R^3$ represents a saturated or unsaturated, straight- or branched chain aliphatic hydrocarbon group having from 1 to 28 carbon atoms, a saturated or unsaturated alicyclic hydrocarbon group having from 3 to 28 carbon atoms or an aromatic hydrocarbon group having from 6 to 28 carbon atoms.

Process B

An alcohol-modified polysiloxane (VIII) is reacted with a carboxylic acid (IV) in the presence of an acid catalyst such as tin chloride, toluenesulfonic acid or the like, or with a carboxylic acid chloride (IX) in the presence of a base such as pyridine to give ester-modified silicone derivative (I).

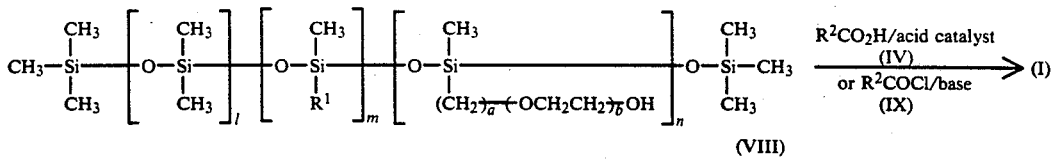

wherein $R^1$, $R^2$, a, b, l, m and n have the meanings respectively defined hereinbefore.

The starting material alcohol-modified polysiloxane (VIII) can be synthesized by reacting the corresponding hydrogenpolysiloxane (II) with an alcohol of formula (V).

The cosmetic composition of the present invention contains the ester-modified silicone derivative (I). While the proportion of (I) in the cosmetic composition is not critical, the preferred range is generally 0.001 to 90% by weight and more preferably 1 to 50% by weight, based on the total weight of the cosmetic composition. The cosmetic composition of the present invention is virtually not limited in form or in type and can be manufactured in a conventional procedure. For example, it can be provided in such varied forms as oily cosmetic products, emulsified cosmetic products, aqueous cosmetic products, lipsticks, foundations, skin hygiene products, shampoos, hair tonics, hair conditioners, hair growth promoting agent and so on.

The ester-modified silicone derivative (I) of the present invention is highly compatible with a silicone oil such as dimethylpolysiloxane, methylphenylpolysiloxane and a cyclic dimethylpolysiloxane; a hydrocarbon oil such as squalane and a liquid paraffin; a polar oil such as isopropyl myristate and various triglycerides; and water, and it helps stabilize systems containing such material as mentioned hereinbefore, so that it is of value as a cosmetic oil over a broad spectrum of uses. Furthermore, the ester-modified silicone derivative (I) of the invention is: (1) liquid at ambient temperature, (2) low in viscosity and less sticky, (3) chemically stable, and (4) only sparingly irritating to the skin, with the result that it is of value as a cosmetic oil for use in applications involving direct contact with the skin.

The cosmetic composition containing the ester-modified silicone derivative (I) in accordance with the present invention insures an improved feeling in use with marked attenuation of the "squeak" which is characteristic of silicone oils.

Having thus, generally described the invention, the following examples illustrating currently preferred modes of practicing the invention are given for purposes of illustration.

EXAMPLE 1

Synthesis of abietic ester-modified silicone (I-a)
(a compound of formula (I) wherein $R^2=$

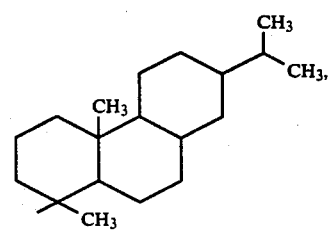

$a=3$, $b=1$, $l=60$ (mean value), $m=0$ and $n=4$ (mean value)):

A 50 ml flask fitted with a condenser, thermometer and stirrer was charged with 20 g (4.1 mmol) of hydrogenpolysiloxane (II-a) (a compound of formula (II) wherein $l=60$ (mean value), $m=0$ and $n=4$ (mean value); manufactured by Toshiba Silicone Co., Ltd.) and 7.0 g (18 mmol) of allyloxyethyl tetrahydroabietate (III-a) followed by the addition of 1.9 mg ($4.4 \times 10^{-3}$ mmol) of chloroplatinic acid hydrate, and the mixture was stirred at 40° C. for 2 hours. After completion of the reaction, the excess ester (III-a) was distilled off under reduced pressure (220° C./0.01 Torr) and the residue was decolorized with activated carbon to give 23 g of the title compound as a colorless oil. IR (liquid film, cm$^{-1}$): 2968, 2872, 1732, 1450, 1416, 1388, 1264, 1098, 1024, 864, 800, 662.

$^1$H-NMR(CDCl$_3$, δ): 4.34–4.14 (m, 8H, CO$_2$-C$\underline{H}_2$2/ —O), 3.60 (t, J=5 Hz, 8H, CO$_2$—C$\underline{H}_2$CH$_2$2/ —O), 3.41 (t, J=7 Hz, 8H, O—C$\underline{H}_2$2/ CH$_2$CH$_2$), 2.11–0.83 (m, about 140 H, CH$_2$2/ C$\underline{H}_2$Si and tetrahydroabietic acid-H), 0.60–0.41 (m, 8H, CH$_2$C$\underline{H}_2$2/ Si), 0.08 (s, about 378H, C$\underline{H}_3$Si).

EXAMPLE 2

Synthesis of Abietic Ester-Modified Silicone (I-b)

(a compound of formula (I) wherein $R^1=C_{16}H_{33}-$ (normal), $R^2=$

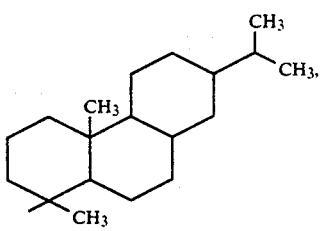

$a=3$, $b=1$, $l=80$ (mean value), $m=12$ (mean value) and $n=8$ (mean value)):

A 100 ml flask fitted with a condenser, thermometer and stirrer was charged with 22 g (3 mmol) of hydrogenpolysiloxane (VI-a) (a compound of formula (VI) wherein $l=80$ (mean value) and $m'+n=20$ (mean value); manufactured by Toshiba Silicone Co., Ltd.) and 8.1 g (36 mmol) of 1-hexadecene (VII-a) followed by the addition of 12 mg of a 2% isopropyl alcohol solution of chloroplatinic acid hydrate ($5.6 \times 10^{-4}$mmol). The mixture was stirred at 50° C. for 2 hours for partial hydrosilylation. To this reaction mixture were added 29 mg (0.3 mmol) of potassium acetate, 15.5 g (30 mmol) of allyloxyethyl tetrahydroabietate (III-a), 30 ml of isopropyl alcohol and 1.3 mg ($3 \times 10^{-3}$ mmol) of chloroplatinic acid hydrate, and the whole mixture was further stirred at 50° C. for 4 hours. Then, 4.0 g (18 mmol) of 1-hexadecene (VII-b) was added and the reaction was further conducted at 50° C. with stirring for 2 hours. From this reaction mixture, the solvent and the excess 1hexadecene (VII-b) and ester (III-a) were distilled off under reduced pressure (230° C./0.01 Torr) and the residue was decolorized with activated carbon to give 30 g of the title compound as a pale yellow oil.

IR (liquid film, cm$^{-1}$): 2964, 2932, 2860, 1732, 1464, 1416, 1388, 1262, 1100, 1020, 804

$^1$H-NMR(CDCl$_3$, δ): 4.35–4.10 (m, 16H, CO$_2$—C$\underline{H}_2$—), 3.62 (t, J=4.7 Hz, 16H, CO$_2$—CH$_2$C$\underline{H}_2$O), 3.42 (t, J=6.9 Hz, 16H, OC$\underline{H}_2$CH$_2$CH$_2$), 2.12–0.74 (m, about 1320H, C$\underline{H}_2$CH$_2$Si, C$\underline{H}_3$(CH$_2$)$_{14}$CH$_2$Si, and tetrahydroabietic acid-H), 0.62–0.42 (m, 40H, —CH$_2$C$\underline{H}_2$Si—), 0.10 (s, about 546H C$\underline{H}_3$—Si).

EXAMPLE 3

Emollient Cream

| Composition: | (% by weight) |
|---|---|
| 1) Compound (I-a) | 10.0 |
| 2) Solid paraffin | 2.0 |
| 3) Cetyl 2-ethylhexanoate | 5.0 |
| 4) Lanolin | 5.0 |
| 5) Beeswax | 2.0 |
| 6) Stearyl alcohol | 4.0 |
| 7) Self-emulsifying glycerol monostearate | 1.5 |
| 8) Polyoxyethylenesorbitan monoleate (20. E.O.) | 1.0 |
| 9) Ethylparaben | an appropriate amount |
| 10) Methylparaben | an appropriate amount |
| 11) Perfume | an appropriate amount |
| 12) Purified water | Balance |
| Total | 100.0 |

Manufacturing Method

Ingredients 1) through 8) were melted by heating and kept at 70° C. Ingredients 9), 10) and 12) were also mixed by heating at 70° C. and the mixture of 1) through 8) was added thereto. The whole mixture was emulsified by means of an emulsifier. The resulting emulsion was allowed to cool with constant stirring to 40° C. and ingredient 11) was added and the system evenly mixed. Using a heat exchanger, the mixture was cooled to 30° C. to give an emollient cream.

This emollient cream had a moist feel but minimum stickiness and was excellent in moisturizing effect and feeling of use.

EXAMPLE 4

Milk Lotion

| Composition: | (% by weight) |
|---|---|
| 1) Compound (I-a) | 1.0 |
| 2) Cetanol | 0.5 |
| 3) Vaseline | 1.0 |
| 4) Squalane | 4.0 |
| 5) Liquid paraffin | 5.0 |
| 6) Stearic acid | 2.0 |
| 7) Polyoxyethylene oleyl ether (20. E.O.) | 2.0 |
| 8) Triethanolamine | 1.0 |
| 9) Ethylparaben | an appropriate amount |
| 10) Perfume | an appropriate amount |
| 11) Purified water | Balance |
| Total | 100.0 |

Manufacturing Method

Ingredients 1) through 7) were melted by heating at 70° C. and homogenously mixed. Ingredients 8), 9) and 11) were also heated at 70° C. and evenly mixed and the mixture of 1) through 7) was gradually added thereto with stirring for emulsification. Using a heat exchanger, the resulting emulsion was cooled to 30° C. and ingredient (0) was added thereto followed by stirring well to give a milk lotion.

This milk lotion had a moist feel with good affinity for the skin and was excellent in feeling upon use.

EXAMPLE 5

Rouge

| Formulation: | (% by weight) |
|---|---|
| 1) Compound (I-a) | 30.0 |
| 2) Carnauba wax | 2.0 |
| 3) Sericin | 4.0 |
| 4) Candelilla wax | 5.0 |
| 5) Microcrystalline wax | 2.0 |
| 6) Beeswax | 3.0 |
| 7) Lanolin | 3.0 |
| 8) Castor oil | 20.0 |
| 9) Hexadecyl alcohol | 20.0 |
| 10) Glycerol monostearate | 2.0 |
| 11) Titanium dioxide | 2.0 |
| 12) Color (Red No. 202) | 2.0 |
| 13) Color (Red No. 204) | 1.0 |
| 14) Color (Yellow No. 4 Al lake) | 3.0 |
| 15) Antioxidant | an appropriate amount |
| 16) Perfume | an appropriate amount |
| Total | 100.0 |

Manufacturing Method

Ingredients 1) through 7), 9) and 10) were melted by heating and a dispersion of 11) through 16) in 8) was added thereto. This mixture was stirred to render the same homogeneous. This mixture was cast in a mold and cooled to give a lipstick.

This lipstick had a moist feel with a minimum of stickiness and provided an excellent feeling upon use.

EXAMPLE 6

Creamy Foundation

| Formulation: | (% by weight) |
|---|---|
| 1) Compound (I-b) | 10.0 |
| 2) Liquid paraffin | 8.0 |
| 3) Squalane | 8.0 |
| 4) Neopentyl glycol dioctanoate | 3.0 |
| 5) Sorbitan sesquiisostearate | 7.0 |
| 6) Aluminum distearate | 0.2 |
| 7) Magnesium sulfate | 0.7 |
| 8) Methylparaben | 0.1 |
| 9) Titanium dioxide | 8.0 |
| 10) Talc | 5.0 |
| 11) Sericite | 2.0 |
| 12) Red oxide | 0.4 |
| 13) Yellow iron oxide | 0.7 |
| 14) Black iron oxide | 0.1 |
| 15) Perfume | an appropriate amount |
| 16) Purified water | Balance |
| Total | 100.0 |

Manufacturing Method

Ingredients 1) through 6) were homogeneously mixed under heating at 70° C. and, then ingredients 9) through 14) were dispersed therein. Ingredients 7), 8) and 16) were then homogeneously mixed at 70° C. and gradually added to the above dispersion with stirring for emulsification. The resulting emulsion was cooled to 40° C. with stirring and ingredient 15) was added thereto. The mixture was further cooled to room temperature with stirring to give a creamy foundation.

This creamy foundation had a moist feel with a minimum of stickiness and provided an excellent feeling upon use.

While the present invention has been described in detail and with reference to specific embodiments thereof, it is apparent to one skilled in the art that various changes and modifications can be made therein without departing form the spirit and the scope of the present invention.

What is claimed is:

1. An ester-modified silicone derivative of formula (I):

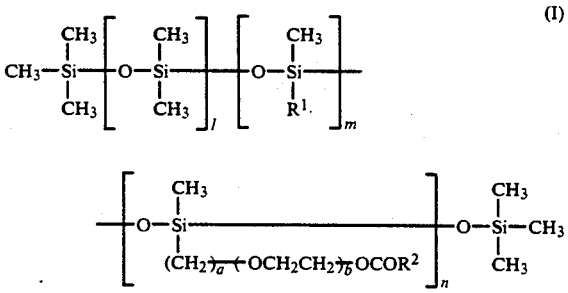

wherein $R^1$ in formula (I) represents a saturated or unsaturated straight- or branched-chain aliphatic hydrocarbon group having from 2 to 30 carbon atoms, a saturated or unsaturated alicyclic hydrocarbon group having from 3 to 30 carbon atoms or an aromatic hydrocarbon group having from 6 to 30 carbon atoms; and $R^2$ in formula (I) represents a group of the formula:

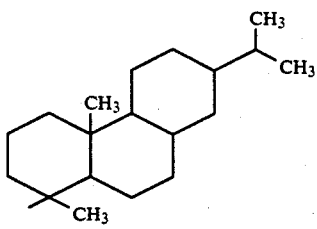

l and m each represents a number of from 0 to 100; n represents a number of from 1 to 100; a represents a number of from 3 to 16; and b represents a number of from 1 to 3.

2. A cosmetic composition containing an ester modified silicone derivative as claimed in claim 1, and a cosmetically acceptable carrier.

* * * * *